US00PP08718P

United States Patent [19]

Zary

[11] Patent Number: Plant 8,718

[45] Date of Patent: May 10, 1994

[54] SHRUB ROSE PLANT NAMED 'JACWHIP'

[75] Inventor: Keith W. Zary, Thousand Oaks, Calif.

[73] Assignee: Bear Creek Gardens, Inc., Medford, Oreg.

[21] Appl. No.: 42,112

[22] Filed: Apr. 2, 1993

[51] Int. Cl.[5] ..... A01H 5/00

[52] U.S. Cl. ..... Plt./1

[58] Field of Search ..... Plt. 1, 23

*Primary Examiner*—Howard J. Locker

*Attorney, Agent, or Firm*—Klarquist, Sparkman, Campbell, Leigh and Whinston

[57] ABSTRACT

A sport of the rose variety JACship having distinct and uniformly white buds and flowers as compared to the pink buds and flowers of its parent.

1 Drawing Sheet

1

The present invention relates to a new and distinct variety of rose plant of the shrub class which was discovered by me by as a mutation of the variety JACship, U.S. Plant Pat. No. 7,948.

The rose plant of the present discovery has a unique combination of characteristics that are outstanding in the new variety and which distinguish it from its parent, as well as from all other varieties of which I am aware. For example, this new rose variety has white buds and flowers rather than the pink buds and flowers of the JACship variety.

Asexual reproduction of this new variety by softwood and hardwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed descriptions of my new rose cultivar with color description using terminology in accordance with The Royal Horticultural Society (London) Colour Chart, except where ordinary dictionary significance of color is indicated.

Classification:

*Botanical.*—Rosa hybrida.

*Commercial.*—Shrub.

FLOWER

Observations made from specimens grown in a garden environment in Somis, Calif., from April through November, 1992.

Blooming habit: Recurrent.

Bud:

*Size.*—½-¾ inches when the petals start to unfurl.

*Form.*—Short, pointed ovoid.

*Color.*—When sepals first divide, bud color is White Group 155D. When half blown, the upper and lower sides of the petals are White Group 155D.

*Sepals.*—Color: Green Group 138C, but often with a bronze cast. Surface texture: Covered in fine hairs. There are three normally appendaged sepals that are edged with glands. There are two unappendaged sepals with hairy edges.

2

*Receptacle.*—Color: Green Group 143C. Shape: Funnel. Size: Small (¼×¼ inch). Surface: Smooth.

*Peduncle.*—Length: Short (1½ to 1¾ inches). Surface: Glandular. Color: Medium green and bronzy. Strength: Stiff, erect, slender.

Bloom:

*Size.*—Small. Average open size is 2 inches.

*Borne.*—Singly, several together, in pyramidal clusters.

*Stems.*—Short (10–12 inches), strong.

Form.—When first open: High centered. Permanence: Retains its form to the end, outer petals curl back, quill fashion.

*Petalage.*—Number of petals under normal conditions: 30–35.

*Color.*—The upper and reverse sides of the petals are White Group 115D. The base of each petal has a small (3/16×4/16 inch), yellow half moon at the point of attachment. The major color on the upper side is White Group 155D.

*Variegations.*—None.

*Discoloration.*—No change in the general tonality at the end of the first day or the third day.

*Fragrance*: Slight.

Petals:

*Texture.*—Thick.

*Shape.*—Round.

*Form.*—Tips slightly recurved, edges slightly quilled.

*Arrangement.*—Imbricatd, with few petaloids in the center.

*Persistence.*—Drop off cleanly.

*Lastingness.*—On the plant: Long (5–7 days). As a cut flower: Long (7 days).

Reproductive parts:

*Anthers.*—Size: Medium. Quantity: Many. Color: Yellow. Arrangement: Regular around styles.

*Filaments.*—Color: Yellow.

*Pollen.*—Color: Gold Yellow.

*Styles.*—Color: Greenish white.

*Stigmas.*—Color: Greenish white.

Form: Shrub.

Growth: Very vigorous, upright, branching.

Foliage: Number of leaflets on normal mid-stem leaves: 5.

*Size.*—Small (3×2 inches).

*Quantity.*—Abundant.

*Color.*—New foliage: Reddish green. Old foliage: Dark green, glossy.

Leaflets:

*Shape.*—Pointed oval.

*Texture.*—Upper side: leathery, glossy.

*Edge.*—Serrated.

*Serration.*—Single, small.

*Petiole rachis.*—Color: Green.

*Petiole underside.*—Rough, with prickles.

*Stipules.*—Long, bearded.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base and on laterals from main canes: Many.

*Form.*—Short (¼ inch), hooked slightly downward.

*Color when young.*—Red.

Small prickles:

*Quantity.*—On main stalks: Many. On laterals: Few.

*Color—Brown.*

I claim:

1. A new and distinct variety of rose plant of the shrub class, substantially as herein shown and described, a sport of the variety JACship, characterized particularly as to novelty by its distinct and uniformly white buds and flowers as compared to the pink buds and flowers of its parent.

* * * * *

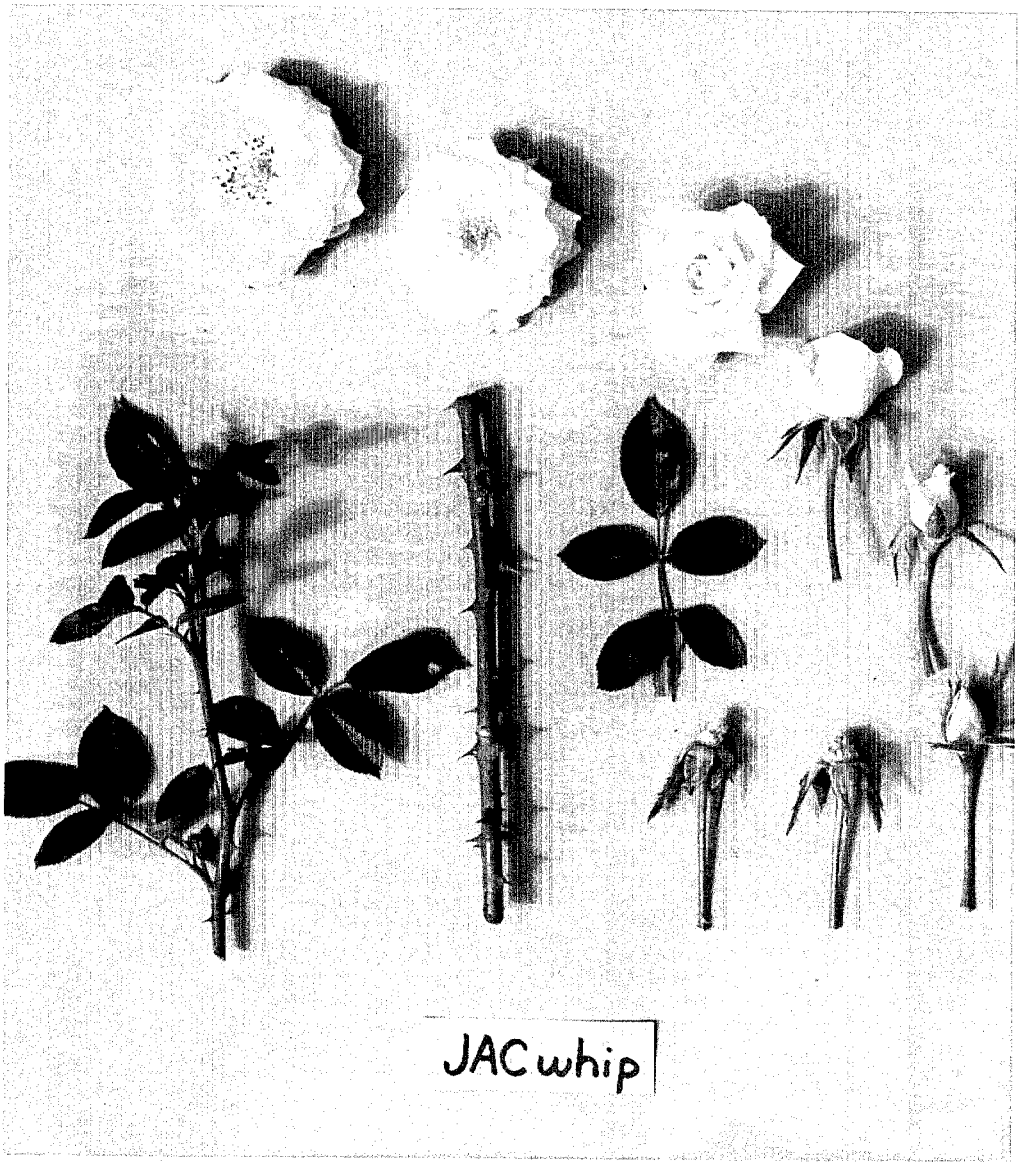
JAC whip

UNITED STATES PATENT AND TRADEMARK OFFICE

CERTIFICATE OF CORRECTION

PATENT NO. : PP 8,718

DATED : May 10, 1994

INVENTOR(S) : Keith W. Zary

It is certified that error appears in the above-identified patent and that said Letters Patent is hereby corrected as shown below:

Column 2, line 18, "115D" should read --155D--.

Signed and Sealed this

Twenty-ninth Day of November, 1994

Bruce Lehman

*Attest:*

BRUCE LEHMAN

*Attesting Officer*

*Commissioner of Patents and Trademarks*